United States Patent [19]
Katz et al.

[11] Patent Number: 5,691,440
[45] Date of Patent: Nov. 25, 1997

[54] CATALYST AND PROCESS FOR PRODUCING ISOCYANATE TRIMERS

[75] Inventors: Lawrence E. Katz, Orange; Edward A. Barsa, Cheshire; Benjamin W. Tucker, Bethany, all of Conn.; Paul V. Grosso, Eagan, Minn.

[73] Assignee: Arco Chemical Technonogy, L.P., Greenville, Del.

[21] Appl. No.: 539,572

[22] Filed: Oct. 5, 1995

[51] Int. Cl.$^6$ ................................................ C08G 18/16
[52] U.S. Cl. ................................. 528/52; 528/44; 528/53; 252/182.2; 544/193; 544/222
[58] Field of Search ................. 528/44, 53, 52; 252/182.2; 544/222, 193

[56] References Cited

U.S. PATENT DOCUMENTS

| | | | |
|---|---|---|---|
| 2,978,449 | 4/1961 | France et al. | 260/248 |
| 3,645,979 | 2/1972 | Liebsch et al. | 260/77.5 NC |
| 3,745,133 | 7/1973 | Comunale et al. | 260/2.5 AW |
| 3,980,594 | 9/1976 | Fabris et al. | 260/2.5 |
| 3,981,829 | 9/1976 | Cenker et al. | 260/2.5 AC |
| 3,993,223 | 11/1976 | Gupta et al. | 260/248 NS |
| 4,040,992 | 8/1977 | Bechara et al. | 260/2.5 AW |
| 4,067,830 | 1/1978 | Kresta | 260/2.5 AW |
| 4,115,373 | 9/1978 | Henes et al. | 528/48 |
| 4,324,879 | 4/1982 | Bock et al. | 528/45 |
| 4,412,073 | 10/1983 | Robin | 544/193 |
| 4,454,317 | 6/1984 | Disteldorf et al. | 544/193 |
| 4,614,785 | 9/1986 | Richter et al. | 528/45 |
| 4,801,663 | 1/1989 | Ueyanagi et al. | 525/528 |
| 4,960,848 | 10/1990 | Schoel | 528/48 |
| 5,070,137 | 12/1991 | Kase et al. | 524/590 |
| 5,124,427 | 6/1992 | Potter et al. | 528/67 |
| 5,436,336 | 7/1995 | Bruchmann | 544/193 |

*Primary Examiner*—Rachel Gorr
*Attorney, Agent, or Firm*—Dale Lynn Carlson; Wiggin & Dana

[57] ABSTRACT

A process for preparing isocyanate adducts having a high proportion of monoisocyanurate using a quaternary ammonium carboxylate trimerization catalyst. Also claimed are specific carboxylate catalysts, together with a process for producing the catalysts. The catalysts are particularly useful for trimerizing hexamethylene diisocyanate and isophorone diisocyanate.

2 Claims, No Drawings

CATALYST AND PROCESS FOR PRODUCING ISOCYANATE TRIMERS

FIELD OF THE INVENTION

This invention relates generally to the production of cyclotrimerized polyisocyanates, and, more specifically, to a process for producing these trimers, novel catalysts useful therein, and a process for making the catalysts.

BACKGROUND OF THE INVENTION

Polyisocyanate adducts, such as, for example, the cyclotrimerized isocyanurate-containing adducts of aliphatic diisocyanates (commonly referred to as trimerized diisocyanates or, in short, "trimers"), as illustrated by isophorone diisocyanate (so-called "IPDI") trimer and hexamethylene diisocyanate (so-called "HDI") trimer, are useful as components of industrial formulations for various coatings applications (e.g., automotive coatings and architectural paints) because they provide good hardness, impact-, solvent-, and abrasion-resistance, and they do not yellow when exposed to sunlight. These trimers are also useful in preparing molded polyurethane and polyurea articles; for example by reaction-injection molding (RIM) processes. Collectively, the various fields of use for these trimers are commonly identified as "ACES", a term that includes adhesives, coatings, elastomers and sealants.

In response to ever-tightening governmental regulation of the presence of volatile organic compounds (so-called "VOCs") such as solvents in formulations for ACES applications, typically needed in order to provide a desirably low viscosity for the formulation, coatings manufacturers are attempting to lower the solvent content of their products in order to provide so-called "low VOC" coating compositions to the marketplace. There is a need in the marketplace for a low VOC coating composition having a solvent content of less than 45%, preferably less than 35%, and most preferably less than 25%, by weight, based upon the weight of the coating composition.

It is not a simple task to provide a low VOC trimer-based coating composition (such as a paint) since, as the solvent content of the coating composition is reduced, the viscosity of the composition increases, thereby causing adverse effects on processability and sprayability of the coating composition, as well as the appearance of the coating after curing.

The catalyst employed to effect the trimerization reaction to produce the trimer can also adversely affect the viscosity of a trimer-containing coating composition if that catalyst is not either deactivated (after production of the trimer), or removed from the trimer product prior to use of the trimer in the coating composition. For example, U.S. Pat. No. 3,980,594 discloses a trimer production process, particularly for trimerizing aromatic isocyanates, using a quaternary ammonium salt of an "organic or inorganic oxygen acid" trimerization catalyst, such as tetramethyl ammonium carbonate, but this patent does not disclose removal or deactivation of the remaining trimerization catalyst residues during or after the trimerization process. Likewise, U.S. Pat. No. 4,040,992 discloses the trimerization of aliphatic diisocyanates using a 2-hydroxyalkyl quaternary ammonium salts of carboxylic acids, but this patent also does not disclose deactivation of the catalyst, or its removal from the trimerized product. The present inventors have found that failure to remove or deactivate these catalyst residues will cause rapid gelation of the crude trimer solution and prevent the eventual production of the final monomer-free trimer product.

There is accordingly a need in the ACES manufacturing industry for isocyanate trimers of IPDI that are of a lower viscosity than those provided to coatings manufacturers in the past, as well as trimers that do not precipitate or gel prior to their use in a coating composition. There is also a need for a low viscosity trimer that is suitable for use in blends with other isocyanates, thereby providing a low viscosity blend. Certain commercially-available catalysts, e.g. DABCO TMR$^R$ which is a quaternary ammonium ethyl hexanoate, tend to cause discoloration of trimers made using this catalyst, particularly HDI trimer as disclosed, for example, at column 2, lines 9–21 of U.S. Pat. No. 5,070,137. The '137 patent attempts to resolve this color problem in HDI trimer-containing compositions by using a trimerization catalyst that is a select N-(2-hydroxyakyl)-quaternary ammonium tertiary aliphatic carboxylate. However, there is a continuing need for other solutions to this color problem for HDI trimer, as well as new catalyst preparation processes.

The present invention provides a solution to each of these needs.

SUMMARY OF THE INVENTION

In one aspect, the present invention relates to a method for producing a high purity trimerization catalyst, useful for trimerizing IPDI or HDI, which comprises the steps of:

(a) haloalkylating a tertiary amine by reacting the tertiary amine with an alkyl halide to provide a quaternary ammonium halide, and (b) reacting said quaternary ammonium halide with a carboxylic acid salt (preferably selected from the group consisting of pivalic acid alkali metal salts, alkaline earth metal salts thereof, 2-ethylhexanoic acid alkali metal salts, alkaline earth metal salts thereof, and combinations thereof) in an ion exchange reaction, in the presence of an organic solvent or on an ion exchange resin, in order to produce the quaternary ammonium carboxylate. It is preferred that the tertiary amine in step (a) contains a hydroxyalkyl group, since hydroxy-containing quaternary ammonium carboxylates can easily be thermally deactivated.

This stops further trimerization after the desired reaction conversion is completed.

A limited number of quaternary ammonium hydroxides are commercially available; these can be titrated with organic acids to yield quaternary ammonium carboxylates.

In another aspect, the present invention relates to an alkyl-substituted quaternary ammonium carboxylate compound containing N-alkyl substitution, said N-alkyl substitution comprising at least one lower alkyl group having between one and five carbons and at least one higher alkyl group having between six and fifty carbons, or at least one hydroxyalkyl group having between 3 and 5 carbons.

In another aspect, the present invention relates to a process for producing low viscosity IPDI trimer. Monomer-free IPDI trimer is a solid at room temperature. To compare IPDI trimer viscosities made by different processes, it is advantageous to compare them either as a 70% solids solution in a suitable solvent or as a 40% trimer solution in monomer. Furthermore, to compare trimer processes, it is advantageous to determine a viscosity as a function of the degree of conversion of the monomer to the trimer. The ideal process is one that has a high conversion of monomer to trimer and yet gives a low viscosity trimer. As with any catalyst, the higher the conversion, the higher the product viscosity due to the formation of increased amounts of higher oligomers. For any given process, the catalysts of the present invention provide a lesser amount of high oligomers, and a lower viscosity product for a given conversion level, as compared to prior art trimerization catalysts. As used herein, the term "high conversion" with respect to IPDI trimer means a conversion to at least about 25% by weight to IPDI trimer for a continuous process, or a conversion to at least about 40% by weight to IPDI trimer for a batch process. The process of the present invention is suitably carried out in batch, continuous or semi-continuous fashion. Illustratively, in a batch process, a crude trimer solution in monomer is suitably produced at about a 40% conversion of monomer to trimer having (after adjustment to 29.6% NCO by addition of IPDI) a Brookfield viscosity not exceeding 1,000 Centipoise (preferably not exceeding 800 cP, more preferably not exceeding 700 cP) at 25° C. The process broadly comprises contacting IPDI with a catalytically effective amount of a quaternary ammonium carboxylate catalyst selected from the group consisting of tetramethylammonium pivalate, tetraethylammonium pivalate, tetrabutylammonium pivalate, tetraoctylammonium pivalate, mixtures of polyoctyl and polydecyl-substituted methylammonium pivalate, methyltrioctylammonium pivalate, 1,-N,N,N-trimethyl-(2-hydroxypropylammonium) pivalate, 1,-N,N,N-trimethyl-(3-hydroxypropylammonium) pivalate, tetramethylammonium 2-ethylhexanoate, tetraethylammonium 2-ethylhexanoate, tetrabutylammonium 2-ethylhexanoate, tetraoctylammonium 2-ethylhexanoate, mixtures of polyoctyl and polydecyl-substituted methylammonium 2-ethylhexanoate, trioctylmethylammonium 2-ethylhexanoate, 1-N,N,N-trimethyl-(2-hydroxypropylammonium)-2-ethylhexanoate, 1-N,N,N-trimethyl-(3-hydroxypropylammonium)-2-ethylhexanoate, and combinations thereof, at a reaction temperature of between about 60° C. and about 130° C. for a reaction time of between a few seconds and about two hours. The reaction is then quenched by addition of a suitable quenching agent or thermally.

In another aspect, the present invention relates to a process for producing low viscosity HDI trimer, having a color of less than 40 APHA units, which comprises contacting HDI with a catalytically effective amount of a quaternary ammonium carboxylate catalyst selected from the group consisting of tetramethylammonium pivalate, tetraethylammonium pivalate, tetrabutylammonium pivalate, tetraoctylammonium pivalate, mixtures of polyoctyl and polydecyl-substituted methylammonium pivalate, methyltrioctylammonium pivalate, 1,-N,N,N-trimethyl-(2-hydroxypropylammonium) pivalate, 1,-N,N,N-trimethyl-(3-hydroxypropylammonium) pivalate, tetramethylammonium 2-ethylhexanoate, tetraethylammonium 2-ethylhexanoate, tetrabutylammonium 2-ethylhexanoate, tetraoctylammonium 2-ethylhexanoate, mixtures of polyoctyl and polydecyl-substituted methylammonium 2-ethylhexanoate, trioctylmethylammonium 2-ethylhexanoate, 1-N,N,N-trimethyl-(2-hydroxypropylammonium)-2-ethylhexanoate, 1-N,N,N-trimethyl-(3-hydroxypropylammonium)-2-ethylhexanoate, and combinations thereof, at a reaction temperature of between about 60° C. and about 130° C. for a reaction time of between a few seconds and about two hours. The reaction is then quenched by the addition of a suitable quenching agent or thermally.

In another aspect, the present invention relates to an N-tetralkyl-substituted quaternary ammonium carboxylate trimerization catalyst, useful for trimerizing aliphatic diisocyanates, selected from the group consisting of polyoctyl-substituted methylammonium carboxylates, polydecyl-substituted methylammonium carboxylates, and combinations thereof. Preferred carboxylates are pivalates, 2-ethylhexanoates, and combinations thereof.

In yet another aspect, the present invention relates to a method of using a compound as a trimerization catalyst, said compound being selected from the group consisting of tetramethylammonium pivalate, tetraethylammonium pivalate, tetrabutylammonium pivalate, tetraoctylammonium pivalate, mixtures of polyoctyl and polydecyl-substituted methylammonium pivalate, methyltrioctylammonium pivalate, 1,-N,N,N-trimethyl-(2-hydroxypropylammonium) pivalate, 1,-N,N,N-trimethyl-(3-hydroxypropylammonium) pivalate, tetramethylammonium 2-ethylhexanoate, tetraethylammonium 2-ethylhexanoate, tetrabutylammonium 2-ethylhexanoate, tetraoctylammonium 2-ethylhexanoate, mixtures of polyoctyl and polydecyl-substituted methylammonium 2-ethylhexanoate, trioctylmethylammonium 2-ethylhexanoate, 1,-N,N,N-trimethyl-(2-hydroxypropylammonium) ethylhexanoate, 1,-N,N,N-trimethyl-(3-hydroxypropylammonium) 2-ethylhexanoate, and combinations thereof, which comprises contacting said compound with a diisocyanate selected from the group consisting of isophorone diisocyanate, hexamethylene diisocyanate, cyclohexane diisocyanate, tetramethylxylene diisocyanate and 4,4'-diisocyanato dicyclohexylmethane, and combinations thereof, at a reaction temperature of between about 60° C. and about 130° C. for a reaction time of between about 5 seconds and about five hours, in order to cause said diisocyanate to cyclotrimerize in the presence of said compound to form a cyclotrimerized trimer product. The reaction is then quenched by addition of a suitable quenching agent or thermally.

In still another aspect, the present invention relates to a low viscosity composition comprising (and advantageously consisting essentially of) IPDI trimer and a suitable carrier selected from the group consisting of an organic solvent, IPDI monomer, and combinations thereof, said composition having a viscosity of between about 500 and about 1,000 centipoise.

In a further aspect, the present invention relates to a low viscosity composition comprising (and advantageously consisting essentially of) low color HDI trimer, having a color of less than 40 APHA units, in the presence or absence of a suitable carrier such as an organic solvent, said low color HDI trimer being prepared by reacting hexamethylene diisocyanate in a cyclization reaction in the presence of a trimerization catalyst selected from the group consisting of tetramethylammonium pivalate, tetraethylammonium pivalate, tetrabutylammonium pivalate, tetraoctylammonium pivalate, mixtures of polyoctyl and polydecyl-substituted methylammonium pivalate, methyltrioctylammonium pivalate, 1,-N,N,N-trimethyl-(2-hydroxypropylammonium) pivalate, 1,-N,N,N-trimethyl-(3-hydroxypropylammonium) pivalate, tetramethylammonium 2-ethylhexanoate, tetraethylammonium 2-ethylhexanoate, tetrabutylammonium 2-ethylhexanoate, tetraoctylammonium 2-ethylhexanoate, mixtures of polyoctyl and polydecyl-substituted methylammonium 2-ethylhexanoate, trioctylmethylammonium 2-ethylhexanoate, 1,-N,N,N-trimethyl-(2-hydroxypropylammonium) ethylhexanoate, 1,-N,N,N-trimethyl-(3-hydroxypropylammonium) 2-ethylhexanoate, and combinations thereof, which comprises contacting said compound with a diisocyanate selected from the group consisting of isophorone diisocyanate, hexamethylene diisocyanate, cyclohexane diisocyanate and tetramethylxylene diisocyanate, and combinations thereof, at a reaction temperature of between about 60° C. and about 130° C. for a reaction time of between about 5 seconds and about five hours. The reaction is then quenched by addition of a suitable quenching agent or thermally.

These and other aspects will become apparent upon reading the following detailed description of the invention.

DETAILED DESCRIPTION OF THE INVENTION

It has now been surprisingly discovered that a trimer can be produced in relatively high yield and purity using a trimerization catalyst within the scope of the present invention. The present invention is especially useful in providing a process for producing trimers of isophorone diisocyanate having a high monoisocyanurate content (at least 70%) and a relatively low viscosity at a relatively high conversion of monomer to trimer. The present invention is useful for the preparation of HDI trimers having a color of less than 40 APHA units and a relatively low viscosity at a relatively high conversion of monomer to trimer.

The trimerization process of the present invention is suitable for use in trimerizing a variety of aliphatic diisocyanates, notably isophorone diisocyanate ("IPDI"), hexamethylene diisocyanate ("HDI"), cyclohexane diisocyanate ("CHDI"), tetramethylxylene diisocyanate ("XDI"), 4,4'-diisocyanato dicyclohexylmethane ("$H_{12}$MDI") and combinations thereof.

In its broadest aspect, the process comprises reacting an aliphatic diisocyanate with a tetraalkylammonium carboxylate of the general formula I, $$R^1R^2R^3R^4\text{-}N^+\ ^-O_2C\text{—}C\text{—}R^5R^6R^7 \qquad I$$

wherein $R^1$, $R^2$, $R^3$ and $R^4$ independently represent a hydrocarbon group containing 1 to 50 carbon atoms, or a hydroxyalkyl group; $R^5$, $R^6$ and $R^7$ independently represent hydrogen or a hydrocarbon group containing 1 to 20 carbon atoms. Preferably, the N-alkyl substitution on the carboxylate comprised of at least one lower alkyl group having between one and five carbons and at least one higher alkyl group having between six and fifty carbons, or at least one 3-hydroxyalkyl group having between 3 and 5 carbons.

After the trimerization reaction is effected to produce the trimer, the catalyst is suitably deactivated either thermally, by elevating the temperature in the reaction mixture to a temperature sufficient to cause degradation of the catalyst, or chemically by the addition of a chemical quenching agent. Suitable chemical quenching agents are those described in the patent literature such as in U.S. Pat. No. 4,324,879 and U.S. Pat. No. 5,070,137. Hydroxy-containing catalysts, such as 2-hydroxy- or 3-(hydroxypropylammonium) carboxylates are highly desirable, because they can be deactivated at a temperature of below 140° C., a temperature low enough to avoid degradation of the trimer product while avoiding the use of a chemical quenching agent. Alternatively, in those cases where the deactivated catalyst is insoluble in the crude trimer solution, the catalyst residue can be removed from the trimer product by precipitation and filtration, if desired. Removal or deactivation of the catalyst is necessary in order to avoid unwanted reaction of the trimer during storage and prior to use in a coating composition. In a continuous process, unreacted aliphatic diisocyanate is suitably removed from the trimer product, for example by distillation, and recycled back to the trimerizing reactor.

Although not wishing to be bound by any particular theory, it is believed that the "water white color" of HDI trimer produced in accordance with the present invention, as compared to HDI trimer available commercially heretofore, is attributable at least in part to the "purer" quality of the quaternary ammonium catalyst typically employed in the present invention.

The isocyanuration catalyst is suitably prepared by a process comprising the steps of:

(a) haloalkylating a tertiary amine by reacting the tertiary amine with an alkyl halide to provide a quaternary ammonium halide, and (b) reacting said quaternary ammonium halide with a carboxylic acid salt (preferably selected from the group consisting of pivalic acid alkali metal salts, alkaline earth metal salts thereof, 2-ethylhexanoic acid alkali metal salts, alkaline earth metal salts thereof, and combinations thereof) in an ion exchange reaction, in the presence of an organic solvent or on an ion exchange resin, in order to produce the desired quaternary ammonium carboxylate.

The use of an ion exchange resin for the production of the trimerization catalyst is preferred, since the resulting trimer catalyst is essentially free of inorganic salt impurities. In contrast, the use of an organic salt for ion exchange from solution causes inorganic salt precipitation, and requires a subsequent filtration to remove inorganic salt impurities from the catalyst.

A limited number of quaternary ammonium hydroxides are commercially available; these can be titrated with organic acids to yield quaternary ammonium carboxylates.

Illustrative examples of suitable isocyanuration catalysts, i.e., the tetraalkylammonium carboxylates, that are useful in the present invention include those represented by structures Ia through Ip, listed below.

| | |
|---|---|
| $(CH_3)_4N^+\ ^-O_2CC(CH_3)_3$ | Ia |
| $(CH_3CH_2)_4N^+\ ^-O_2CC(CH_3)_3$ | Ib |
| $(CH_3CH_2CH_2CH_2)_4N^+\ ^-O_2CC(CH_3)_3$ | Ic |
| $(C_8H_{17})_4N^+\ ^-O_2CC(CH_3)_3$ | Id |
| $(C_8H_{17})_2(C_{10}H_{21})(CH_3)N^+\ ^-O_2CC(CH_3)_3$ | Ie |

Representing the Aliquat® 336 cation

| | |
|---|---|
| $(C_8H_{17})_3(CH_3)N^+\ ^-O_2CC(CH_3)_3$ | If |
| $(CH_3CH(OH)CH_2)(CH_3)_3N^+\ ^-O_2CC(CH_3)_3$ | Ig |
| $(HOCH_2CH_2CH_2)(CH_3)_3N^+\ ^-O_2CC(CH_3)_3$ | Ih |
| $(CH_3)_4N^+\ ^-O_2CCH(C_2H_5)(CH_2)_3CH_3$ | Ii |
| $(CH_3CH_2)_4N^+\ ^-O_2CCH(C_2H_5)(CH_2)_3CH_3$ | Ij |
| $(CH_3CH_2CH_2CH_2)_4N^+\ ^-O_2CCH(C_2H_5)(CH_2)_3CH_3$ | Ik |
| $(C_8H_{17})_4N^+\ ^-O_2CCH(C_2H_5)(CH_2)_3CH_3$ | Il |
| $(C_8H_{17})_2(C_{10}H_{21})(CH_3)N^+\ ^-O_2CCH(C_2H_5)(CH_2)_3CH_3$ | Im |

Representing the Aliquat® 336 cation

| | |
|---|---|
| $(C_8H_{17})_3(CH_3)N^+\ ^-O_2CCH(C_2H_5)(CH_2)_3CH_3$ | In |
| $(CH_3CH(OH)CH_2)(CH_3)_3N^+\ ^-O_2CCH(C_2H_5)(CH_2)_3CH_3$ | Io |
| $(HOCH_2CH_2CH_2)(CH_3)_3N^+\ ^-O_2CH(C_2H_5)(CH_2)_3CH_3$ | Ip |

Ia: Tetramethylammonium pivalate
Ib: Tetraethylammonium pivalate
Ic: Tetrabutylammonium pivalate Id: Tetraoctylammonium pivalate
Ie: Mixture of polyoctyl or polydecyl-substituted methylammonium pivalate (Aliquat 336 pivalate)
If: Methyltrioctylammonium pivalate
Ig: 1-N,N,N-Trimethyl-(2-hydroxy-propylammonium) pivalate
Ih: 1-N,N,N-Trimethyl-(3-hydroxy-propylammonium) pivalate
Ii: Tetramethylammonium 2-ethylhexanoate
Ij: Tetraethylammonium 2-ethylhexanoate
Ik: Tetrabutylammonium 2-ethylhexanoate
Il: Tetraoctylammonium 2-ethylhexanoate
Im: Mixture of polyoctyl or polydecyl-substituted methylammonium 2-ethylhexanoate (Aliquat$^R$ 336 2-ethylhexanoate
In: Trioctylmethylammonium 2-ethylhexanoate
Io: 1-N,N,N-Trimethyl-(2-hydroxy-propylammonium) 2-ethylhexanoate
Ip: 1-N,N,N-Trimethyl-(3-hydroxy-propylammonium) 2-ethylhexanoate The amount of catalyst employed in the trimerization process of the present invention (on an active catalyst basis) is preferably between 10 and 200 ppm, more preferably between 10 and 100 ppm, most preferably between 50 and 80 ppm, in the reaction mixture containing the diisocyanate monomer to be trimerized. The above-described broadest range on amount of catalyst (which is equivalent to between 0.02 and 0.001 weight percent, based upon the weight of the reaction mixture), facilitates a desirably rapid trimerization reaction rate and the production of a desirably low-color trimer product. Reaction temperature may vary between 60° C. and 130° C., but is preferably between 75° C. and 100° C., and most favorably between 80° and 90° C. Co-catalysts and co-reactants such as monols and diols may optionally be employed in the trimerization process of the present invention if desired. Useful supplemental trimerization catalysts include the following: phosphines as described in U.S. Pat. No. 3,645,979; phosphorus acid triamides as described in U.S. Pat. No. 4,614,785; aminosilyl catalysts such as aminosilanes, diaminosilanes, silylureas, and silazanes as described in U.S. Pat. No. 4,412,073; alkali alcoholates and phenolates, alkali carboxylates and alkali hydroxides as described in U.S. Pat. No. 2,978,449; tertiary amines as described in U.S. Pat. No. 3,745,133 and U.S. Pat. No. 3,981,829, aminimides as described in U.S. Pat. No. 4,067,830; quaternary ammonium carboxylates as described in U.S. Pat. No. 4,454,317 and U.S. Pat. No. 4,801,663; quaternary ammonium hydroxides as described in U.S. Pat. No. 4,324,879 and U.S. Pat. No. 5,124,427; Mannich bases, such as those based on monylphenol, formaldehyde and dimethylamine as described in U.S. Pat. No. 3,996,223 and U.S. Pat. No. 4,115,373; and the like. The supplemental catalyst (if used) is suitably employed in an amount of between about 0.01% and about 0.5%, based upon the weight of the coating composition. If co-reactants, such as alcohols, are employed in the trimerization reaction mixture, additional catalysts known to promote the reaction of isocyanates with the co-reactants may be employed, if desired.

The trimer products produced in accordance with the present invention are useful in a variety of so-called "one-component" and "two-component" coating compositions that contain very low amounts of volatile organic compounds ("VOCs"), are moisture or heat curable, have an excellent color of less than 40 APHA, and are useful for coating a wide variety of substrates.

The diisocyanates suitable for use in the trimerization process of the present invention is suitably any aliphatic diisocyanate (a term intended to include cycloaliphatic diisocyanates), such as, for example, 4,4'-diisocyanato-dicyclohexylmethane, hexamethylene diisocyanate, and 1-isocyanato-3,3,5-tri-methyl-5-isocyanatomethyl-cyclohexane, 1,4-butanediisocyanate, 1-methyl-2,4-diisocyanato-cyclohexane, 1-methyl-2,6-diisocyanatocyclohexane, 4,4'-methylene-bis(cyclohexyl isocyanate), 2-methyl-1,5-diisocyanatopentane, 2-ethyl-1,4-diisocyanatobutane, 2,4,4-trimethylhexamethylene-1,6-diisocyanate, a,a'-diisocyanato-1,3-dimethylcyclohexane, a,a'-diisocyanato-1,4-dimethylcyclohexane, 1,3-diisocyanatocyclohexane, and 1,4-diisocyanatocyclohexane wherein "a" denotes "alpha". HDI and IPDI are the most preferred starting materials for the preparation of the trimerized polyisocyanates.

The trimers prepared in accordance with the present invention are useful in various coating compositions, such as heat- or moisture-curable coating compositions. In preparing heat curable coating compositions, blocking agents are suitably employed to block one or more of the isocyanate groups on the polyisocyanate if desired. Heat unblocking of the polyisocyanate is then effected at the desired temperature as a prelude to the coating formation. Suitable blocking agents include those well-known in the art, for example, aromatic alcohols such as phenol, cresols, trimethyl phenols and tert-butyl phenols; tertiary alcohols such as tert-butanol, tert-amyl alcohol, and dimethyl phenyl carbinol; compounds which readily form enols such as ethyl acetoacetate, acetyl acetone and malonic acid diethyl ester; secondary aliphatic and aromatic amines such as dibutyl amine, N-methyl aniline, the N-methyl toluidines, N-phenyl toluidine and N-phenyl xylidine; imides such as succinimide; lactams such as e-caprolactam and d-valerolactam; oximes such as butanone oxime and cyclohexanone oxime; mercaptans, such as methyl mercaptan, ethyl mercaptan, butyl mercaptan, 2-mercapto-benzothiazole, alpha-naphthyl mercaptan and dodecyl mercaptan; triazoles such as 1-H-1,2,4-triazole; and pyrazoles such as 3,5-dimethylpyrazole, 3-methylpyrazole, 4-nitro-3,5-dimethylpyrazole, and 4-bromo-3,5-dimethylpyrazole.

The coating compositions containing trimers produced in accordance with the present invention suitably contain small quantities of isocyanate-inert solvents in amounts of between 0% and 45% by weight, based upon the weight of the coating composition. It is preferred to minimize the amount of solvent utilized in the coating compositions of the present invention in order to minimize the VOC of the coating composition itself. However, some amount of solvent may be required in order to provide a desired low viscosity. Suitable solvents include toluene, xylene, butyl acetate, methyl ethyl ketone, methyl isobutyl ketone, methylamyl ketone, ethylethoxy propionate, ethoxyethylacetate, an aromatic hydrocarbon mixture having a boiling point of 152°–174° C., combinations thereof, and the like. Other optional additives are suitably employed, if desired, such as, for example, uv stabilizers; leveling agents; flow-aids; pigments, such as titanium dioxide; plasticizers; and/or other resins.

The coating compositions containing trimers produced in accordance with the present invention are suitable for use in the production of clear or pigmented coatings, and may be applied to a desired substrate by conventional methods, such as spread coating, roller application or spraying. Because of the low viscosity of the compositions of the present invention, they are especially suitable for application by conventional spray techniques. The coating thickness on the substrate can vary over a wide range, although a dry film coating thickness of between about 0.01 and 0.5 millimeters is preferred.

Substrates for the coating useful in the present invention are suitably selected from a wide range of materials such as other plastics, such as polyethylene or polystyrene, wood and paper substrates, and metal substrates, such as sheet steel or aluminum.

The coating compositions are stable in storage when heat and moisture are excluded and they harden under the influence of heat and/or moisture to form coatings. As stated above, when hardening or curing of the coatings on the substrate in accordance with the invention is carried out by exposure to heat, the temperature employed is between 120° F. and 350° F. for a curing time of between about ten minutes and about six hours. When curing is effected by exposure to moisture, an ambient or elevated temperature is suitably employed using a curing time of between about ten minutes and about six hours.

The coating compositions, resulting from the use of isocyanate adducts of the present invention, are suitable for use in the production of automotive clear coatings or undercoats, floor covering coatings, wall coatings, transportation coatings, maintenance coatings, and the like, or any other application where a low VOC coating composition is desired for use on a substrate.

While the invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

The following examples are intended to illustrate, but in no way limit the scope of, the present invention.

EXAMPLE 1

Trimerization of Isophorone Diisocyanate (IPDI)

IPDI monomer (710 g) was placed in a 1 liter four-neck Morton flask, equipped with a nitrogen inlet, mechanical stirrer, condenser, and thermocouple. The reactor was heated, with vigorous stirring under a nitrogen purge, to 85° C. The catalyst, for example Aliquat 336 pivalate (Ie), (0.2 g of a 40% solution) in triethylene glycol monomethyl ether, was added in small portions to maintain 85° C. After about two hours, a sample that was analyzed via FTIR indicated 43.4% conversion. At this point the catalyst was quenched by addition of hydrochloric acid. The 700 g of reaction product was nearly colorless. The product was defined via G.P.C, viscosity, and % NCO. The viscosity was 2200 cP; % NCO was 28.6. The product was diluted to 29.6% NCO by addition of 84.7 g IPDI monomer. The viscosity of the final diluted product was 730 cP. The oligomer distribution, as determined by GPC, was: 78.3% trimer; 16.4% pentamer; 5.3% heptamer and higher oligomers.

EXAMPLE 2–10

Trimerization of Isophorone Diisocyanate (IPDI) Using Various Tetraalkylammonium Carboxylate Catalysts The following series of examples illustrates the range of catalysts that may be used to produce IPDI trimers with a high level of monoisocyanurate. Viscosities are given for each product solution.

| Example # | Catalyst | % Conv. | Viscosity of prod. soln, cP | Trimer % | Pentamer % | Heptamer & higher, % |
|---|---|---|---|---|---|---|
| 2 | Ie | 27 | 670 | 85.5 | 11.5 | 2.0 |
| 3 | Ie | 40 | — | 81.3 | 15.2 | 3.5 |
| 4 | Ie | 44 | 730 | 78.3 | 16.4 | 5.3 |
| 5 | Ie | 57 | — | 73.5 | 19.8 | 6.8 |
| 6 | Io | 30 | 920 | 81.1 | 14.4 | 4.5 |
| 7 | Ia | 41 | — | 76.9 | 17.4 | 5.8 |
| 8 | Io | 45 | — | 71.4 | 20.1 | 8.5 |
| 9 | Ip | 39 | — | 49.1 | 28.2 | 22.8 |
| 10 | Ig | 45 | — | 71.4 | 20.1 | 8.5 |

COMPARATIVE EXAMPLE 1

Trimerization of Isophorone Diisocyanate (IPDI) Using Potassium Pivalate Catalyst A procedure similar to Example 1 was followed, substituting potassium pivalate for the tetraalkylammonium carboxylate catalyst. The results are listed below.

| % Conv. | Viscosity of prod. soln., cP | Trimer % | Pentamer % | Heptamer & higher, % |
|---|---|---|---|---|
| 30 | 1200 | 51.9 | 27.1 | 19.6 |

COMPARATIVE EXAMPLE 2–3 AND EXAMPLE 11

Comparison to Commercially Available Trimers of Isophorone Diisocyanate

The table compares conventional products viscosity to a similar product made by the instant invention.

| Source of IPDI trimer | Trimer % | Pentamer % | Heptamer & higher, % | Brookfield viscosity cP |
|---|---|---|---|---|
| Hüls 1890L* | 66.0 | 21.7 | 12.3 | 1175 |
| Miles Z-4370** | 53.6 | 23.4 | 17.6 | 2035 |
| Ie*** | 76.9 | 17.8 | 5.3 | 850 |

*70% solution in butyl acetate/Aromatic 100, 1:2
**70% solution in Aromatic 100
***70% solution in butyl acetate/Aromatic 100, 1:2

COMPARATIVE EXAMPLE 4 AND EXAMPLES 12–13

Trimerization of Isophorone Diisocyanate Using Various Tetraalkylammonium Carboxylate Catalysts The table below illustrates the improved storage stability imparted to crude trimer product when catalysts prepared by the processes of this invention, imparts to crude IPDI trimer, as well as IPDI that can be recovered from the crude reaction mixture.

The procedure of example 1 was followed, except when the desired trimer conversion were attained the catalyst was deactivated by heating to 130°.

| Example # | Catalyst | Unstripped | Recovered Monomer |
|---|---|---|---|
| Comp. Ex. 4 | DABCO TMR$^R$-2 | TD | TD |
| Example 12 | Io* | TD | FP |
| Example 13 | Ie | C | C |

Notes:
TD = turbidity developed
FP = fine precipitate
C = clear
DABCO TMR$^R$-2:80% N-(2-hydroxypropyl)N,N,N-trimethylammonium 2-ethlthexanoate in dipropylene glycol
*Made using the procedure of U.S. 4,040,992. Alkoxylation of trimethylamine with propylene oxide in the presence of 2-ethylhexanoic acid. Solution in diethylene glycol monomethyl ether.

EXAMPLE 12

Preparation of Tetraalkylammonium Carboxylate Catalysts

A) Methylation of Tertiary amines

1) Iodomethylation Procedure: Trioctylmethylammonium Iodide

Trioctylamine (7.00 g), methanol (20 ml), and methyl iodide (5.50 g) were placed in a 50 ml "Hypovial". The vial (equipped with a magnetic stirrer) was sealed under nitrogen, stirred at ambient temperature for 19 hours, and than at 90° C. for 3 hours. Volatiles were evaporated and the product dried in vacua. The product, 9.90 g (quantitative), was a light yellow solid; assay for iodide: 25.5% (99.6%).

2) Chloromethylation Procedure: 1-N,N,N-Trimethyl-(2-hydroxypropylammonium) chloride 1-dimethylamino-2-propanol (103.5 g), methanol (372.0 g), and methyl chloride (57.9 g) were placed in a 2 liter pressure vessel. The vessel (with a magnetic stirrer) was sealed and stirred at ambient temperature for 16.5 hours. Volatiles were removed, in vacua, using a rotary evaporator, and the product dried in a vacuum oven. The product, 155.0 g (98.8%), was a white solid; assay for chloride: 22.65% (98.2%).

B) Cation Exchange of Tetraalkylammnonium Salts

1) Via Ion Exchange Resin: Trioctylmethylammonium Pivalate

Dowex 1X8-50 (50 ml) was placed in a column, and 180 ml of 2M sodium hydroxide percolated through. Then a series of liquids were percolated through: 750 ml water; 980 g 2% pivalic acid in water; 1 liter water; 190 g methanol. Finally, trioctylmethylammonium iodide (3.20 g) in methanol (36 g) was percolated through the column, followed by 82 g methanol. The combined methanol eluate was rotary evaporated, in vacua, to give 3.03 g (94.7%) of the product as a waxy solid; assay for pivalate: 2.13 meq/g (99.4%).

2) Via Cation Exchange in solution: 1-N,N,N-Trimethyl-(2-hydroxypropylammonium)Pivalate 1-N,N,N-trimethyl-(2-hydroxypropylammonium) chloride (77.2 g) and methanol (77.0 g) were placed in a 500 ml flask (equipped with a stirrer). To this stirred solution was added 150.0 g of potassium pivalate in methanol (44.7%), and the mixture stirred for one hour. Filtration yielded 38.0 g (102%) of potassium chloride (dried), and filtrate. The filtrate was rotary evaporated, in vacua, to give 107.8 g (101%) of the product as a solid; assay for pivalate: 4.6 meq/g (95.0%).

C) Neutralization with Carboxylic Acids

1) Titration: Tetramethylammonium 2-ethylhexanoate

Tetramethylammonium hydroxide pentahydrate (90.5 g), 2-ethylhexanoic acid (75.2 g), and triethyleneglycol monomethyl ether (157.6 g) were stirred for 0.5 hour. The reaction mixture was rotary evaporated, in vacua, to give 264.2 g of light yellow solution; assay for 2-ethylhexanoate: 1.87 meq/g (102.0%).

TABLE I

| | | | Quaternary Ammonium Catalysts $R_1R_2R_3R_4N^+X^-$ | | | |
|---|---|---|---|---|---|---|
| Name (#) | $R_1$ | $R_2$ | $R_3$ | $R_4$ | Salt | Proced.* |
| Tetramethyl | $CH_3$ | $CH_3$ | $CH_3$ | $CH_3$ | Pivilate | B2, C1 |
| | | | | | 2-Ethyl-hexanoate | C1 |
| Choline | $CH_3$ | $CH_3$ | $CH_3$ | $CH_2CH_2OH$ | Pivilate | B2 |
| | $CH_3$ | $CH_3$ | $CH_3$ | $CH_2CCH_3$<br>\|<br>OH | Pivilate | A1, A2, B1, B2 |
| TMR$^R$ | $CH_3$ | $CH_3$ | $CH_3$ | $CH_2CCH_3$<br>\|<br>OH | 2 Ethyl-hexanoate | |
| TMR$^R$-2 | $CH_3$ | $CH_3$ | $CH_3$ | $CH_2CCH_3$<br>\|<br>OH | Formate | |
| | Et | Et | Et | Et | Pivilate | C1 |
| | | | | | 2-Ethyl-hexanoate | C1 |

TABLE I-continued

| Name (#) | R₁ | R₂ | R₃ | R₄ | Salt | Proced.* |
|---|---|---|---|---|---|---|
| Tetrabutyl | n-Bu | n-Bu | n-Bu | n-Bu | Pivilate | C1 |
| | | | | | 2 Ethyl-hexanoate | C1 |
| Barquat$^R$ CT-29 | CH₃ | CH₃ | CH₃ | CH₃(CH₂)₁₅ | Pivilate | B2 |
| Bardac$^R$ 2280 | CH₃ | CH₃ | CH₃(CH₂)₉ | CH₃(CH₂)₉ | Pivilate | B2 |
| Barquat$^R$ CME-35 | Et | CH₃(CH₂)₁₅ | -(CH₂)₅- | | Pivilate | B2 |
| Aliquat$^R$ 336 | CH₃ | CH₃(CH₂)₇ | CH₃(CH₂)₇ | CH₃(CH₂)₇ | Pivilate | B1, B2 |
| | CH₃ | CH₃(CH₂)₉ | CH₃(CH₂)₉ | CH₃(CH₂)₉ | 2 Ethyl-hexanoate | B1, B2 |
| Trioctyl-Methyl | CH₃ | CH₃(CH₂)₇ | CH₃(CH₂)₇ | CH₃(CH₂)₇ | Pivilate | A1, B1 |
| Arquad$^R$ 316 | CH₃ | CH₃(CH₂)₁₅ | CH₃(CH₂)₁₅ | CH₃(CH₂)₁₅ | Pivilate | B2 |

*Note: Procedures used employ the acid (or acid salt) corresponding to the product listed in the table.

EXAMPLE 13

Trimerization of 1,6-Hexamethylene Diisocyanate (HDI) Using a Quencher

HDI monomer (800 g) was placed in a 1 liter flask, equipped with a nitrogen inlet and mechanical stirrer; this was set up and heated as described in example 1. The catalyst, 0.1–0.2 g of 40%, (see Table I for a list of these) was added in small portions, to maintain the reaction temperature at 85° C. The reaction was followed by FTIR; the appropriate amount of quencher was added when the desired conversion was achieved. The crude reaction mixture was filtered, and stripped on a wiped film evaporator. The product was defined via color, viscosity, and G.P.C.

| # Catalyst Used | Conversion | Stripped Product Color (via Nessler Tubes) |
|---|---|---|
| (1) Choline Pivalate* | 36% | 90 APHA |
| (2) Ig* | 34% | 65 APHA |
| (3) Ig | 40% | 10 APHA |
| (4) Ie | 41% | 25 APHA |

* = made by the procedure of U.S. PAT. NO. 4,040,992; others made by the processes of example 12.

EXAMPLE 14

Thermally Quenched

Reaction was carried out as in example 13, except the temperature was 115° C. The catalyst, 1-N,N,N-trimethyl-(2-hydroxypropylammonium) 2-ethylhexanoate (Io), was made according to example 12 A1 and B2. A 40% solution of this catalyst was added to HDI, as described in example 13, to attain a 30% conversion. The reaction mixture was then heated to 135° C., to deactivate the catalyst, and the mixture stripped on a wiped film evaporator. The final color was 10 APHA (via Nessler Tubes).

COMPARATIVE EXAMPLE 5

The procedure of example 14 was followed, except DABCO TMRR[1-N,N,N-trimethyl-2-hydroxypropylammonium (2-ethylhexanoate), Io] was employed. The final color was 60 APHA (via Nessler Tubes).

COMPARATIVE EXAMPLE 6

Three portions of DABCO TMR$^R$, 10% in triethylene glycol monomethyl ether, were stirred with 10% of various carbons* at 40° C. for an hour. The procedure of example 14, employing these treated DABCO TMR$^R$ solutions as catalyst, was than carried out. The color of the stripped trimer was not improved by any of the carbon treatments. This shows that impurities in this commercially available catalyst, believed to cause color, can not be removed; the unique performance of catalysts prepared by the processes of this invention can not be attained by using chemically similar commercial catalysts.

*Darco$^R$S51FF, Nuchar$^R$ SA20, Norit$^R$ A.

EXAMPLE 15

Trimerization of Isophorone Diisocyanate Using Several Tetraalkylammonium Carboxylate Catalysts The procedure of example 1 was followed except instead of adding a chemical quenching agent the reaction mixture was heated to 130° C. to deactivate the catalyst.

| Example # | Catalyst | Conversion | Color (APHA) |
|---|---|---|---|
| 15a | Ig | 38.9 | 5 |
| 15b | Ip | 42.7 | 6 |

EXAMPLE 16

Thermally Quenched

Reaction was carried out as in example 14, except the catalyst used was 1-N,N,N-trimethyl-(2-hydroxypropylammonium) pivalate (Ig), made according to example 12 A1 and B2. A 40% solution of this catalyst was added to HDI, as described in example 13, to attain a 30% conversion. The reaction mixture was then heated to 135° C., to deactivate the catalyst, and the mixture stripped on a wiped film evaporator. The final color was 10 APHA (via Nessler Tubes).

This example illustrates the excellent color of HDI trimer obtained when the hydroxypropylammonium quaternary catalysts of the present invention are employed.

COMPARATIVE EXAMPLE 7

Chemically Quenched (This is the procedure of U.S. Pat. No. 5,070,137 example 1)

The procedure of example 16 was followed, except that when the mixture attained a 30% conversion, the required amount of chloroacetic acid (5% in xylene) was added (to deactivate the catalyst). The reaction mixture was cooled to room temperature, and then stripped on a wiped film evaporator. The final color was >200 APHA (yellow).

EXAMPLE 17

Chemically Quenched

The procedure of example 13 was followed, except that tetrabutylammonium pivalate (Ic) was used, when the mixture attained a 30% conversion, the required amount of hydrochloric acid was added. The reaction mixture was then cooled to room temperature, filtered, and stripped on a wiped film evaporator. The final color was 8 APHA; this trimer was a clear water-white liquid and remained so upon storage.

COMPARATIVE EXAMPLE 8

Not Quenched (This is the procedure of U.S. Pat. No. 3,980,594)

The procedure of example 13, using catalyst Ie, was followed, except that when the mixture attained a 30% conversion, the reaction was cooled to room temperature. Within 0.5 hour, the reaction mixture gelled, making the trimer unusable.

Notes:

A) Conversion of monomeric diisocyanate to trimer was determined by two methods.

1. FTIR Method: Absorbance at 1693 $cm^{-1}$/Absorbance at 2951 $cm^{-1}$=Y $Y=mX+b$ Where X=% conversion/100; m and b are determined using standards.

Used a Perkin-Elmer 1600 FTIR or a Nicolet 205 FTIR for these analyses.

2. GPC Method: Conversion calculated using standards.

B) Turbidity: A "clear" solution has less than 2.0 NTU of turbidity.

Used a Hach Ratio Turbidimeter for these analyses.

C) Color was determined by two methods; method 1 was used for all examples, unless otherwise specified. Color should only be compared when the same method was used.

1. Color True—Procedure code C.11, Hach DR/3000 manual #19600-22 (12-01-91-9ED). From: Standard Methods for the Examination of Water and Wastewater, $15^{th}$ edition (1980).

Used a Hach DR/3000 Spectrophotometer for these analyses.

This gives color in APHA units which are the same as Hazen color units.

2. Nessler Color Comparison Method—ASTM D1209

D) Viscosity was determined using a Brookfield DV-II viscometer; using the appropriate spindles and Brookfield viscosity standards.

EXAMPLE 18–22

Trimerization of Hexamethylene Diisocyanate Using Various Tetraalkylammonium Carboxylate Catalysts The following series of examples illustrates the range of catalysts that may be used to produce HDI trimers with excellent color. The procedure of example 16 was followed.

| Example # | Catalyst | Conversion | Color |
|---|---|---|---|
| 18 | Io | 33.4 | 9 |
| 19 | Io | 32.5 | 5 |
| 20 | Ig | 34.7 | 3 |
| 21 | Im | 32.6 | 6 |
| 22 | Ia | 32.4 | 8 |

EXAMPLE 23

1-N,N,N-Trimethyl-(2-hydroxypropylammonium) 2-Ethylhexanoate

A-Via Ion Exchange Resin:

The procedure of example 12 B1 was carried out using 2-ethylhexanoic acid in isopropanol to load the ion exchange resin. A solution of 1-N,N,N-Trimethyl-(2-hydroxypropylammonium) chloride in methanol was percolated through the column. Rotary evaporation, and trituration with ether, gave a 95% yield of a thick amber liquid; assay for 2-ethylhexanoate: 3.73 meq/g (97.9%) via titration, and 97.2% via FTNMR.

B-Via cation Exchange:

1-N,N,N-Trimethyl-(2-hydroxypropylammonium) chloride (21.9 g) and methanol (21.9 g) were placed in a 200 ml flask (equipped with a stirrer). To this stirred solution was added 70.0 g of potassium 2-ethylhexanoate in methanol (from 20.4 g 2-ethylhexanoic acid, 20.0 g methanol, and 29.9 g of 26.5% potassium hydroxide) and the mixture stirred for one hour. After filtration, rotary evaporation of the filtrate yielded a light yellow liquid. This was diluted with methanol, filtered, rotary evaporated in vacua, to give 33.8 g of viscous light yellow oil; assay for 2-ethylhexanoate: 3.63 meq/g (95.2%).

COMPARATIVE EXAMPLE 9

(Example 7 from U.S. Pat. No. 4,040,992)

Methylamine (60.0 g, 1.0 mole) was bubbled into 144 g (1.0 mole) of 2-ethylhexanoic acid; to the mixture was added 58.0 g (1.0 mole) of propylene oxide and stirring continued 18 hours. The resulting clear viscous liquid was assayed via NMR analysis: 75.0%. When this catalyst was employed in the processes of this invention, the color of trimer produced was darker than when the same catalyst made via either of the above procedures was used.

Although not wishing to be bound by any specific theory, it is believed that the improvement in color and storage stability of trimer, when 1-N,N,N-trimethyl hydroxypropylammonium quaternary catalysts which were prepared via methylation are used, is due to the high purity of the quaternary ammonium catalyst. The starting amine was purified by distillation, methylation was essentially quantitative, and ion exchange goes cleanly (especially when an ion exchange resin was used). Catalysts made via ion exchange resin contain no potassium or chloride, trimer made from them are less likely to develop any cloudiness or precipitates upon storage.

What is claimed is:

1. A product mixture produced by a process which comprises contacting isophorone diisocyanate with a catalytically effective amount of between 10 ppm and 100 ppm of a quaternary ammonium carboxylate catalyst selected from the group consisting of tetramethylammonium pivalate, tetraethylammonium pivalate, tetrabutylammonium pivalate, tetraoctylammonium pivalate, mixtures of polyoctyl and polydecyl-substituted methylammonium pivalate, methyltrioctylammonium pivalate, tetramethylammonium 2-ethylhexanoate, tetraethylammonium 2-ethylhexanoate, tetrabutylammonium 2-ethylhexanoate, tetraoctylammonium 2-ethylhexanoate, mixtures of polyoctyl and polydecyl-substituted methylammonium 2-ethylhexanoate, trioctylmethylammonium 2-ethylhexanoate, and combinations thereof, at a reaction temperature of between about 60° C. and about 130° C. for a reaction time of between about five seconds and about two hours, to produce isophorone diisocyanate trimer in said product mixture containing higher oligomers of isophorone diisocyanate, said product mixture being characterized by a monomeric trimer content of at least 70% based upon the weight of the product mixture and a Brookfield viscosity not exceeding 800 Centipoise at 25° C. as determined by diluting the product mixture with IPDI monomer to an NCO concentration of 29.6%.

2. A low viscosity composition comprising isophorone diisocyanate trimer and a suitable solvent selected from the group consisting of an organic solvent, isophorone diisocyanate monomer, and combinations thereof, said composition having a Brookfield viscosity of between about 500 and about 800 Centipoise at a temperature of 25° C. as determined by diluting said isophorone diisocyanate trimer with said carrier to an NCO concentration of 29.6%, said isophorone trimer being prepared by cyclizing isophorone diisocyanate monomer in the presence of between 10 ppm and 100 ppm of a quaternary ammonium carboxylate trimerization catalyst selected from the group consisting of tetramethylammonium pivalate, tetraethylammonium pivalate, tetrabutylammonium pivalate, tetraoctylammonium pivalate, mixtures of polyoctyl and polydecyl-substituted methylammonium pivalate, methyltrioctylammonium pivalate, tetramethylammonium 2-ethylhexanoate, tetraethylammonium 2-ethylhexanoate, tetrabutylammonium 2-ethylhexanoate, tetraoctylammonium 2-ethylhexanoate, mixtures of polyoctyl and polydecyl-substituted methylammonium 2-ethylhexanoate, trioctylmethylammonium 2-ethylhexanoate, and combinations thereof, which comprises contacting said catalyst with said isophorone diisocyanate monomer at a reaction temperature of between about 60° C. and about 130° C. for a reaction time of between about five seconds and about five hours, to provide a product mixture containing trimer, and deactivating trimerization catalyst in said product mixture with a chemical quenching agent, or by heating said product mixture to a temperature sufficient to thermally deactivate said catalyst in said product mixture.

* * * * *